United States Patent
Uchiyama et al.

(10) Patent No.: US 8,329,154 B2
(45) Date of Patent: *Dec. 11, 2012

(54) COMPOSITIONS COMPRISING A DISPERSANT AND MICROCAPSULES CONTAINING AN ACTIVE MATERIAL

(75) Inventors: Hirotaka Uchiyama, Loveland, OH (US); Jonathan Robert Cetti, Mason, OH (US); Mario Alonso, Loveland, OH (US); David Lee Montezinos, Hamilton, OH (US); Daniel Scott Cobb, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1265 days.

This patent is subject to a terminal disclaimer.

(21) Appl. No.: 11/487,549

(22) Filed: Jul. 14, 2006

(65) Prior Publication Data

US 2006/0258768 A1    Nov. 16, 2006

Related U.S. Application Data

(63) Continuation of application No. 10/405,678, filed on Apr. 2, 2003, now abandoned.

(60) Provisional application No. 60/373,439, filed on Apr. 18, 2002.

(51) Int. Cl.
*A61L 9/00* (2006.01)
*C08K 9/10* (2006.01)

(52) U.S. Cl. ............... 424/76.2; 424/76.3; 424/76.8; 428/402.21; 523/102; 523/205

(58) Field of Classification Search .......... 424/76.8, 424/76.2, 76.3; 523/102, 205; 428/402.21
See application file for complete search history.

(56) References Cited

U.S. PATENT DOCUMENTS

| | | |
|---|---|---|
| 4,145,184 A | 3/1979 | Brain et al. |
| 4,520,142 A | 5/1985 | Leinen |
| 4,946,624 A | 8/1990 | Michael |
| 5,143,949 A * | 9/1992 | Grogan et al. ............ 523/334 |
| 5,256,328 A | 10/1993 | Cavanagh et al. |
| 5,425,887 A | 6/1995 | Lam et al. |
| 5,591,146 A | 1/1997 | Hasse |
| 5,663,134 A | 9/1997 | Trinh et al. |
| 5,783,544 A | 7/1998 | Trinh et al. |
| 5,788,975 A | 8/1998 | Laversanne et al. |
| 5,861,144 A | 1/1999 | Peterson et al. |
| 5,929,053 A | 7/1999 | Murakami et al. |
| 6,248,364 B1 | 6/2001 | Sengupta et al. |
| 6,333,022 B1 * | 12/2001 | Tanaka ....................... 424/45 |
| 7,226,607 B2 * | 6/2007 | Uchiyama et al. ......... 424/401 |
| 2003/0215417 A1 | 11/2003 | Uchiyama et al. |

FOREIGN PATENT DOCUMENTS

| | | |
|---|---|---|
| EP | 0 385 534 | 9/1990 |
| FR | 2685857 | 7/1993 |
| JP | 03173565 A * | 7/1991 |
| WO | WO 98/26808 | 6/1998 |
| WO | WO 98/56340 | 12/1998 |
| WO | WO 99/35120 | 12/1998 |
| WO | WO 00/46337 | 8/2000 |

OTHER PUBLICATIONS

Full English language translation of JP 03-173565 A, Jul. 26, 1991.*
Hawley's Condensed Chemical Dictionary, 14th Edition, 2002.

* cited by examiner

*Primary Examiner* — Vickey Nerangis
(74) *Attorney, Agent, or Firm* — Amy I Ahn-Roll; Leonard W Lewis

(57) ABSTRACT

Compositions for providing controlled-release of an active material comprise a dispersant and microcapsules containing the active material. The compositions contain the dispersant and/or microcapsules at relatively low levels to avoid negatively impacting the surfaces treated with the compositions. The active material is preferably a perfume and the composition provides a controlled-release scent, along with controlling malodor when the compositions fuirther comprise optional odor control agent. Methods of providing a controlled-release of an active material on a surface comprise the step of contacting the surface with a composition comprising a dispersant and microcapsules containing an active material.

30 Claims, No Drawings

COMPOSITIONS COMPRISING A DISPERSANT AND MICROCAPSULES CONTAINING AN ACTIVE MATERIAL

CROSS REFERENCE TO RELATED APPLICATION

This application is a continuation of U.S. application Ser. No. 10/405,678, filed Apr. 2, 2003 now abandoned which claims priority to U.S. Provisional Application Ser. No. 60/373,439 filed Apr. 18, 2002, the disclosure of which is incorporated by reference herein.

TECHNICAL FIELD

The present invention relates to compositions that can be applied to surfaces, including household surfaces such as carpets, fabrics, and the like, for providing a controlled-release of an active material, preferably a perfume scent, into the environment surrounding the surface.

BACKGROUND OF THE INNENTION

Fabric refresher products have become a popular product in today's consumer goods market. Such products typically involve a liquid composition that is sprayed onto surfaces, such as fabrics, to reduce or remove malodor from the surfaces. Some of these products can also provide a pleasing scent by incorporation of perfume into the composition. However, such products typically are not capable of providing a controlled-release of an active material, such as a perfume scent.

Other products merely provide a pleasant fragrance, but do not act to reduce or remove malodor. Instead, such products utilize strong perfume scents to mask malodors by providing a scent stronger than the malodor. JP 03-173,565 ("JP '565") discloses an encased-perfume spray composition wherein the perfume is encased in microcapsules. The spray composition is preferably an aerosol-type composition utilizing a propellant. The perfume-encased microcapsules adhere to clothes, carpets, neckties, etc., and the fragrance is slowly released or is released by pressure such as friction. The spray compositions of JP '565 provide a pleasant fragrance, but contain relatively high levels of microcapsules and/or binder that can negatively impact the surface being treated.

JP 11-246383 ("JP '383") similarly discloses a composition made of a slurry of microcapsules containing essential oils mixed with an aqueous binder. The compositions can be applied to fibers, such as bedding sheets, in which the fragrance can be released from the microcapsule, e.g., during movement as a person sleeps. However, as with the spray compositions of JP '565, the compositions of JP '383 provide a pleasant fragrance, but contain relatively high levels of microcapsules and/or binder that can negatively impact the surface being treated.

U.S. Pat. No. 4,520,142 ("US '142") discloses microencapsulated liquids, such as perfumes, that are applied to substrates from an aerosol applicator. The aerosol compositions of US '142 contain a microcapsule containing liquid, a polymeric binder, a solvent for the polymeric binder, and an aerosol propellant. However, while the aerosol compositions of US '142 provide a controlled-release of a liquid material, the compositions contain relatively high levels of microcapsules and/or binder that can negatively impact the surface being treated.

There has thus been a need to provide a composition that is able to provide a controlled-release of an active material, preferably a perfume scent, into the environment surrounding the surface without negatively impacting the treated surface. There has been a further need to provide a composition that is able to provide a controlled-release of an active material and kill microorganisms on a surface being treated with the composition. The present invention addresses these previously unmet needs.

SUMMARY OF THE INVENTION

The present invention relates to compositions (non-aerosol and aerosol) comprising a dispersant, microcapsules containing an active material and/or an optional odor control agent (which may be referred to herein as an "encapsulated odor control agent"), and aqueous carrier. The compositions contain relatively low levels of dispersant and/or microcapsules to avoid negatively impacting the treated surface. The compositions can be applied to surfaces, such as fabrics, to provide a controlled-release of the active material onto the surface or into the environment surrounding the surface. The active material is preferably a perfume and the composition provides a controlled-release scent.

The invention further relates to antimicrobial compositions comprising a dispersant, microcapsules containing an active material and/or an optional odor control agent, an antimicrobial active, and aqueous carrier.

The invention further relates to methods of using these compositions comprising the step of contacting a surface with the compositions.

The invention further relates to a process for making a composition comprising a dispersant and microcapsules containing an active material.

The present invention further relates to the use of a composition comprising a dispersant and microcapsules containing an active material to provide a controlled-release of the active material onto a surface or into the environment surrounding the surface.

All documents cited herein are, in relevant part, incorporated herein by reference; the citation of any document is not to be construed as an admission that it is prior art with respect to the present invention.

It should be understood that every maximum numerical limitation given throughout this specification will include every lower numerical limitation, as if such lower numerical limitations were expressly written herein. Every ninimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified.

DETAILED DESCRIPTION OF THE INVENTION

The compositions of the present invention comprise microcapsules containing an active material (preferably perfume) and/or an optional odor control agent (which may be referred to herein as an "encapsulated odor control agent"), a dispersant, and aqueous carrier. The present compositions can also contain a wide variety of additional optional ingredients such as odor control agents, solvents, aerosol propellants, surfactants, free perfume, antimicrobial actives/preservatives, wrinkle control agents, and the like. The compositions herein include both non-aerosol and aerosol compositions. The compositions can be used to provide a controlled-release of the active material and/or an optional odor control agent. When the active material is a perfume, the present compositions provide a controlled-release scent.

It should be understood that the active material need not be completely encapsulated (that is, in some embodiments, it may be partially encapsulated). The same is true for the microcapsules containing the encapsulated odor control agent.

There are a non-limiting number of embodiments of the compositions described herein. These embodiments include, but are not limited to embodiments in which at least some of the same microcapsules contain both an active material and the optional odor control agent therein. In other embodiments, the composition may comprise a group of microcapsules that contain an active material, and different microcapsules that contain the optional odor control agent. The composition may comprise microcapsules with different types of shells or coating materials. In addition, in some embodiments, the encapsulated odor control agent and the odor control agent outside of the microcapsules may be the same odor control agent. In other embodiments, they may be different odor control agents.

The present compositions preferably comprise microcapsules and/or dispersants at relatively low levels to avoid negatively impacting the surface being treated with the compositions. For example, if the compositions contain too high an amount of microcapsules and/or dispersants, there can be a potential problem with the composition leaving an undesirable and visible residue on the surface being treated with the compositions. Furthermore, if the surface is fabric and the composition has too high an amount of dispersant, the composition can cause the fabric to become undesirably stiff and/or less soft to the touch.

Microcapsules Containing an Active Material

The present compositions comprise microcapsules containing an active material and/or an optional odor control agent. The microcapsules provide a controlled-release of the active material and/or an optional odor control agent contained in the microcapsule. The microcapsules in the compositions of the present invention can be any ruptureable capsule containing an active material and/or an optional odor control agent therein or capsule which is controllably penetrable by the active material and/or an optional odor control agent encapsulated therein. The rupture strength of the microcapsules should be within a range that can endure handling and spraying without rupturing and yet break by applying a force of friction across the surface being treated with the composition.

The shell of the microcapsules can be made from a wide variety of materials. Such materials are typically polymeric and are designed to resist becoming solubilized in the chemical matrix of the present compositions. Non-limiting examples of materials suitable for making the shell of the microcapsules herein include urea-formaldehydes, melamineformaldehydes, phenolformaldehydes, gelatin, poly(vinyl alcohol), poly(vinyl pyrrolidone), polyacrylates, polyamides, polyurethane, polymethacrylates, polyepoxides, cellulose acetate, cellulose nitrate, cellulose acetate butyrate, ethyl cellulose polyester, polychlorotrifluoroethylene (e.g. KEL-F), ethyl/vinyl acetate, saran, polystyrene, zein, paraffin wax, animal wax, vegetable wax, microcrystalline wax, polyethylene wax, and the like. Preferred microcapsule shell materials include poly(oxymethyleneurea), poly(oxymethylenemelamine), gelatin, polyurethane, poly(vinyl alcohol), and mixtures thereof. Other suitable microcapsule shell materials are disclosed in, e.g., U.S. Pat. Nos. 2,800,458; 3,159,585; 3,516,846; 3,533,958; 3,697,437; 3,888,689; 3,996,156; 3,965,033; 4,010,038; 4,016,098; 4,087,376; 5,591,146; UK Patent Nos. 2,006,709 and 2,062,570; and Benita, Simon (ed.), MICROENCAPSULATION: METHODS AND INDUSTRIAL APPLICATIONS (Marcel Dekker, Inc. 1996).

The size of the microcapsules can be important in the usefulness of microcapsules according to the practice of the present invention. Generally, the microcapsules will have an average diameter of from about 0.001 to about 1,000 microns, preferably from about 1 to about 500 microns, more preferably from about 10 to about 100 microns, and even more preferably from about 20 to about 70 microns. These dimensions can play an important role in the ability to control the application of capsules in the practice of the present invention. The broadest range of capsule size under any conditions would be about 0.001 to about 1,000 microns and a more easily sprayed size limit would be between about 20 and about 70 microns.

In general, the present compositions can comprise microcapsules at a wide variety of levels. Microcapsules are typically included in the present compositions at a level of from about 0.001% to about 99.9%, preferably from about 0.005% to about 50%, and more preferably from about 0.01% to about 20%, by weight of the composition. When the compositions are aqueous liquid compositions (especially non-aerosol compositions) to be sprayed onto surfaces, such as fabrics, the compositions will preferably comprise less than about 1%, preferably less than about 0.9%, more preferably less than about 0.5%, and even more preferably less than about 0.2%, by weight of the composition, of microcapsules. If the level of microcapsules is too high, the compositions may leave a visible residue on the surface being treated. In addition, if the surface is fabric and the level of microcapsules is too high, the fabric appearance may be altered. Furthermore, if the active material is perfume and the level of microcapsules is too high, the initial perfume "burst" when the product is sprayed onto the surface may be unpleasant to the consumer, since the force of the spray tends to rupture some of the microcapsules.

A variety of processes known in the art can be used to make the microcapsules herein. Examples of processes for making microcapsules are described in U.S. Pat. Nos. 2,800,458; 3,159,585; 3,516,846; 3,516,941; 3,533,958; 3,697,437; 3,778,383; 3,888,689; 3,965,033; 3,996,156; 4,010,038; 4,016,098; 4,087,376; 4,089,802; 4,100,103; 4,251,386; 4,269,729; 4,303,548; 4,460,722; and 4,610,927; UK Patent Nos. 1,156,725; 1,483,542; 2,041,319 and 2,048,206; and Benita, Simon (ed.), MICROENCAPSULATION: METHODS AND INDUSTRIAL APPLICATIONS (Marcel Dekker, Inc. 1996).

The active material can be a wide variety of materials in which one would want to deliver in a controlled-release manner onto the surfaces being treated with the present compositions or into the environment surrounding the surfaces. Non-limiting examples of active materials include perfumes, flavoring agents, fungicide, brighteners, antistatic agents, wrinkle control agents, fabric softener actives, hard surface cleaning actives, skin and/or hair conditioning agents, antimicrobial actives, UV protection agents, insect repellants, animal vermin repellants, flame retardants, and the like.

In a preferred embodiment, the active material is a perfume, in which case the microcapsules containing perfume provide a controlled-release scent onto the surface being treated or into the environment surrounding the surface. In this case, the perfume can be comprised of a number of perfume raw materials known in the art, such as essential oils, botanical extracts, synthetic perfume materials, and the like.

In general, the active material is contained in the microcapsule at a level of from about 1% to about 99%, preferably from about 10% to about 95%, and more preferably from about 30% to about 90%, by weight of the total microcapsule. The weight of the total microcapsule includes the weight of the shell of the microcapsule plus the weight of the material inside the microcapsule. The encapsulated odor control agent, if present may be contained in mirocapsules at the same range of levels. Of course if both active material and an odor control agent are contained in the same microcapsule, the total percentage of these components will never exceed 100%.

Microcapsules containing an active material, preferably perfume, suitable for use in the present compositions are described in detail in, e.g., U.S. Pat. Nos. 3,888,689; 4,520,142; 5,126,061; and 5,591,146.

Dispersants

The present compositions further comprise a dispersant. A dispersant can be important to suspend the microcapsules in the composition to prevent the microcapsules from falling out of solution. Thus a dispersant can be important in achieving a composition that is stable.

When the present compositions are designed to be sprayed from a spray dispenser, it can be important to select a level and type of dispersant that provides enough suspension for microcapsule particles, but at the same time is easily sprayable as a fine mist. Some dispersants are capable of suspending particles, but result in compositions having viscosities that are too high to be easily sprayable as a fine mist.

In this respect, the level and type of dispersant is preferably selected to provide a non-Newtonian viscosity property. The resulting malodor-controlling compositions thus will preferably have a difference of viscosity at shear rate 1 $sec^{-1}$ and at 10 $sec^{-1}$ of at least about 0.1 centipoise, preferably at least about 0.5 centipoise, and more preferably at least about 1 centipoise. In this regard, the compositions herein are preferably shear-thinning. The resulting compositions are capable of adequately suspending particles therein (e.g. microcapsules) while being easily sprayable from a spray dispenser.

The preferred dispersants herein provide a shear-thinning composition having a weak gel formation maxtrix, in which polymeric or non-polymeric ingredients interact with each other and form hydrogen and/or hydrophobic bonding. Some functional groups on the molecules have electrostatic repulsive forces that can prevent coagulation of the particles in the composition. The weakly formed gel matrix resulting from the preferred dispersants herein is capable of suspending micron size particles, such as microcapsules, in the composition matrix.

When present, dispersants are typically included at a level of from about 0.001% to about 10%, preferably from about 0.005% to about 5%, and more preferably from about 0.01% to about 1%, by weight of the composition. If it is desired to keep the viscosity of the present compositions relatively low, e.g. if the compositions are to be sprayed onto surfaces (e.g. fabrics) via a spray dispenser, the dispersant is preferably included at a level of less than about 1%, more preferably less than about 0.9%, and even more preferably less than about 0.8%, by weight of the composition. If the level of dispersant is too high, the composition may leave a visible residue on the treated surfaces. If the composition is to be sprayed on fabrics and the level of dispersant is too high, the composition may undesirable alter the fabric feel or softness.

The dispersants herein can be selected from materials such as pectine, alginate, arabinogalactan, carageenan, gellan gum, xanthum gum, guar gum, acrylates/acrylic polymers, water-swellable clays, fumed silicas, acrylate/aminoacrylate copolymers, and mixtures thereof. Preferred dispersants herein include those selected from the group consisting of acrylate/acrylic polymers, gellan gum, fumed silicas, acrylate/aminoacrylate copolymers, water-swellable clays, and mixtures thereof.

Acrylate/acrylic polymers include acrylic emulsion terpolymers. These types of dispersants are typically alkali activated. Suitable alkali activated acrylate/acrylic polymers are described in detail in U.S. Pat. Nos. 5,990,233 and 5,840,789. Such alkali activated acrylate/acrylic polymer dispersants are available from Alco Chemical under the trade name ALCOGUM® SL series.

Gellan gum is a heteropolysaccharide prepared by fermentation of Pseudomonaselodea ATCC 31461. Gellan gum is available from CP Kelco U.S., Inc. under various names, including KELCOGEL®, KELCOGEL® LT100, KELCOGEL® AFT, KELCOGEL® AF, KELCOGEL® PC, and KELCOGEL® F. Processes for preparing gellan gum are described in U.S. Pat. No. 4,326,052 (Kang et al), issued Apr. 20, 1982; U.S. Pat. No. 4,326,053 (Kang et al), issued Apr. 20, 1982; U.S. Pat. No. 4,377,636 (Kang et al), issued Mar. 22, 1983; and U.S. Pat. No. 4,385,123 (Kang et al), issued May 24, 1983.

Fumed silicas are a colloidal form of silica made by combustion of silicon tetrachloride in hydrogen-oxygen furnaces. Fumed silicas are known by the chemical name silicium dioxide. Fumed silicas suitable in the present compositions are available from Degussa AG under the tradename AEROSIL®. A preferred fumed silica is AEROSIL®200 (available from Degussa AG), which is a hydrophilic fumed silica having a specific surface area of about 200 $m^2$/gram.

Acrylate/aminoacrylate copolymers are typically aqueous dispersions of an amine functional acrylic polymer rheology modifier. These types of dispersants are typically acid activated, as compared to acrylate/acrylic polymer dispersants described hereinbefore which are typically alkali activated. Acrylate/arninoacrylate copolymers are available from Alco Chemical under the trade name ALCOGUM® L-500 series. Preferred acrylate/aminoacrylate copolymers are ALCOGUM® L-511 and ALCOGUM® L-520 which are aqueous dispersions of amine functional acrylic polymers available from Alco Chemical.

Water-swellable clays include hectorites and synthetic layered silicates. Synthetic layered silicates are available from Southern Clay Products, Inc. under the trade name LAPONITE®. These synthetic layered silicates are layered hydrous magnesium silicates, in which magnesium ions, partially replaced by suitable monovalent ions such as lithium, sodium, potassium and/or vacancies, are octahedrally coordinated to oxygen and/or hydroxyl ions, some of which may be replaced by fluorine ions, forming the central octahedral sheet, the octahedral sheet being sandwiched between two tetrahedral sheets of silicon ions, tetrahedrally coordinated to oxygen. Preferred synthetic layered silicates include LAPONITE® RD and LAPONITE® RDS available from Southern Clay Products, Inc. Hectorites are available from Rheox, Inc. under the trade name BENTONE®. These hectorites are prepared by reacting bentonite in a cation exchange system with an amine. Preferred hectorites include BENTONE® LT and BENTONE® AD available from Rheox, Inc.

Aqueous Carrier

The aqueous carrier of the present invention comprises water. The water which is used can be distilled, deionized, or tap water. Water not only serves as the liquid carrier for the microcapsules, but it also facilitates the reaction between the odor control agents and any unwanted molecules on surfaces, such as malodorous molecules that are on inanimate surfaces such as fabric, when the surface is treated. It has been found that the intensity of unwanted malodorous molecules generated by some polar, low molecular weight organic amines, acids, and mercaptans is reduced when the malodor-contaminated surfaces are treated with an aqueous solution. It is believed that water solubilizes and depresses the vapor pressure of these polar, low molecular weight organic molecules, thus reducing their odor intensity.

The level of aqueous carrier in the present compositions can vary dependent upon the use of the composition. In general, the level of aqueous carrier in the present compositions can be from about 0.1% to about 99.9%. In compositions designed to be sprayed from manually or non-manually operated spray dispensers, the level of aqueous carrier is preferably high, for example, at a level of at least about 80%, preferably at least about 85%, more preferably at least about 90%, and even more preferably at least about 95%, by weight of the composition.

Optional Ingredients

The present compositions can further comprise a wide variety of optional ingredients, such as odor control agents, solvents, aerosol propellants, surfactants, free perfume, preservatives/antimicrobial actives, wrinkle control agents, and the like.

Odor Control Agents

The present compositions optionally, but preferably, further comprise one or more odor control agent(s) at a level of from about 0.001% to about 99.99%, preferably from about 0.002% to about 99.9%, and more preferably from about 0.005% to about 99%, by weight of the malodor-controlling composition. When the compositions are aqueous liquid compositions (especially non-aerosol compositions) to be sprayed onto surfaces, such as fabrics, the compositions will preferably comprise less than about 20%, preferably less than about 10%, more preferably less than about 5%, by weight of the composition, of odor control agent. The odor control agent serves to reduce or remove malodor from the surfaces or objects being treated with the present compositions. The odor control agent is preferably selected from the group consisting of: uncomplexed cyclodextrin; odor blockers; reactive aldehydes; flavanoids; zeolites; activated carbon; and mixtures thereof. Compositions herein that comprise odor control agents can be used in methods to reduce or remove malodor from surfaces treated with the compositions.

Uncomplexed Cyclodextrin

As used herein, the term "uncomplexed cyclodextrin" includes any of the known cyclodextrins in uncomplexed form such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in donut-shaped rings. The specific coupling and conformation of the glucose units give the cyclodextrins a rigid, conical molecular structures with hollow interiors of specific volumes. The "lining" of each internal cavity is formed by hydrogen atoms and glycosidic bridging oxygen atoms; therefore, this surface is fairly hydrophobic. The unique shape and physical-chemical properties of the cavity enable the cyclodextrin molecules to absorb (form inclusion complexes with) organic molecules or parts of organic molecules which can fit into the cavity. Many odorous molecules can fit into the cavity including many malodorous molecules and perfume molecules. Therefore, cyclodextrins, and especially mixtures of cyclodextrins with different size cavities, can be used to control odors caused by a broad spectrum of organic odoriferous materials, which may, or may not, contain reactive functional groups. The complexation between cyclodextrin and odorous molecules occurs rapidly in the presence of water. However, the extent of the complex formation also depends on the polarity of the absorbed molecules. In an aqueous solution, strongly hydrophilic molecules (those which are highly water-soluble) are only partially absorbed, if at all. Therefore, cyclodextrin does not complex effectively with some very low molecular weight organic amines and acids when they are present at low levels on surfaces.

The cavities within the cyclodextrin in the deodorizing composition of the present invention should remain essentially unfilled (the cyclodextrin remains uncomplexed) while in solution, in order to allow the cyclodextrin to absorb various odor molecules when the solution is applied to a surface. Non-derivatised (normal) beta-cyclodextrin can be present at a level up to its solubility limit of about 1.85% (about 1.85 g in 100 grams of water) under the conditions of use at room temperature.

Preferably, the cyclodextrin used in the present invention is highly water-soluble such as, alpha-cyclodextrin and/or derivatives thereof, gamma-cyclodextrin and/or derivatives thereof, derivatised beta-cyclodextrins, and/or mixtures thereof. The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a —$CH_2$—CH(OH)—$CH_3$ or a —$CH_2CH_2$—OH group; branched cyclodextrins such as maltose-bonded cyclodextrins; cationic cyclodextrins such as those containing 2-hydroxy-3-(dimethylamino)propyl ether, wherein R is $CH_2$—CH(OH)—$CH_2$—$N(CH_3)_2$ which is cationic at low pH; quaternary ammonium, e.g., 2-hydroxy-3-(trimethylammonio)propyl ether chloride groups, wherein R is $CH_2$—CH(OH)—$CH_2$—$N^+(CH_3)_3Cl^-$; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49; and mixtures thereof. Other cyclodextrin derivatives are disclosed in U.S. Pat. No: 3,426,011, Parmerter et al., issued Feb. 4, 1969; U.S. Pat. Nos. 3,453,257; 3,453,258; 3,453,259; and 3,453,260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,678,598, Ogino et al., issued Jul. 7, 1987; U.S. Pat. No. 4,638,058, Brandt et al., issued Jan. 20, 1987; and U.S. Pat. No. 4,746,734, Tsuchiyama et al., issued May 24, 1988. Further cyclodextrin derivatives suitable herein include those disclosed in V. T. D'Souza and K. B. Lipkowitz, CHEMICAL REVIEWS: CYCLODEXTRINS, Vol. 98, No. 5 (American Chemical Society, July/August 1998).

Highly water-soluble cyclodextrins are those having water solubility of at least about 10 g in 100 ml of water at room temperature, preferably at least about 20 g in 100 ml of water, more preferably at least about 25 g in 100 ml of water at room temperature. The availability of solubilized, uncomplexed cyclodextrins is essential for effective and efficient odor control performance. Solubilized, water-soluble cyclodextrin can exhibit more efficient odor control performance than non-water-soluble cyclodextrin when deposited onto surfaces, especially carpeted surfaces.

Examples of preferred water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, and hydroxypropyl beta-cyclodextrin. Hydroxyalkyl cyclodextrin derivatives preferably have a degree of substitution of from about 1 to about 14, more preferably from about 1.5 to about 7, wherein the total number of OR groups per cyclodextrin is defined as the degree of substitution. Methylated cyclodextrin derivatives typically have a degree of substitution of from about 1 to about 18, preferably from about 3 to about 16. A known methylated beta-cyclodextrin is heptakis-2,6-di-O-methyl-β-cyclodextrin, commonly known as DIMEB, in which each glucose unit has about 2 methyl groups with a degree of substitution of about 14. A preferred, more commercially available, methylated beta-cyclodextrin is a randomly methylated beta-cyclodextrin, commonly known as RAMEB, having different degrees of substitution, normally of about 12.6. RAMEB is more preferred than DIMEB, since DIMEB affects the surface activity of the preferred surfactants more than RAMEB. The preferred cyclodextrins are available, e.g., from Cerestar USA, Inc. and Wacker Chemicals (USA), Inc.

It is also preferable to use a mixture of cyclodextrins. Such mixtures absorb odors more broadly by complexing with a wider range of odoriferous molecules having a wider range of molecular sizes. Preferably at least a portion of the cyclodextrin is alpha-cyclodextrin and its derivatives thereof, gamma-cyclodextrin and its derivatives thereof, and/or derivatised beta-cyclodextrin, more preferably a mixture of alpha-cyclodextrin, or an alpha-cyclodextrin derivative, and derivatised beta-cyclodextrin, even more preferably a mixture of derivatised alpha-cyclodextrin and derivatised beta-cyclodextrin, most preferably a mixture of hydroxypropyl alpha-cyclodextrin and hydroxypropyl beta-cyclodextrin, and/or a mixture of methylated alpha-cyclodextrin and methylated beta-cyclodextrin.

Since cyclodextrin can be a prime breeding ground for certain microorganisms, especially when in aqueous compositions, it is preferable to include a water-soluble preservative, as described infra, which is effective for inhibiting and/or regulating microbial growth, to increase storage stability of aqueous odor-absorbing solutions containing water-soluble cyclodextrin.

Odor Blockers

"Odor blockers" can be used as an odor control agent to mitigate the effects of malodors. In order to be effective, the odor blockers normally have to be present at all times. If the odor blocker evaporates before the source of the odor is gone, it is less likely to control the odor. Also, the odor blockers can tend to adversely affect aesthetics by blocking desirable odors like perfumes.

Non-limiting examples of odor blockers suitable as odor control agents in the present compositions include 4-cyclohexyl-4-methyl-2-pentanone, 4-ethylcyclohexyl methyl ketone, 4-isopropylcyclohexyl methyl ketone, cyclohexyl methyl ketone, 3-methylcyclohexyl methyl ketone, 4-tert.-butylcyclohexyl methyl ketone, 2-methyl4-tert.butylcyclohexyl methyl ketone, 2-methyl-5-isopropylcyclohexyl methyl ketone, 4-methylcyclohexyl isopropyl ketone, 4-methylcyclohexyl sec.butyl ketone, 4-methylcyclohexyl isobutyl ketone, 2,4-dimethylcyclohexyl methyl ketone, 2,3-dimethylcyclohexyl methyl ketone, 2,2-dimethylcyclohexyl methyl ketone, 3,3-dimethylcyclohexyl methyl ketone, 4,4-dimethylcyclohexyl methyl ketone, 3,3,5-trimethylcyclohexyl methyl ketone, 2,2,6-trimethylcyclohexyl methyl ketone, 1-cyclohexyl-1-ethyl formate, 1-cyclohexyl-1-ethyl acetate, 1-cyclohexyl-1-ethyl propionate, 1-cyclohexyl-1-ethyl isobutyrate, 1-cyclohexyl-1-ethyl n-butyrate, 1-cyclohexyl-1-propyl acetate, 1-cyclohexyl-1-propyl n-butyrate, 1-cyclohexyl-2-methyl-1-propyl acetate, 2-cyclohexyl-2-propyl acetate, 2-cyclohexyl-2-propyl propionate, 2-cyclohexyl-2-propyl isobutyrate, 2-cyclohexyl-2-propyl n-butyrate, 5,5-dimethyl-1,3-cyclohexanedione (dimedone), 2,2-dimethyl-1,3-dioxane-4,6-dione (Meldium's acid), spiro-[4.5]-6,10-dioxa-7,9-dioxodecane, spiro-[5.5]-1,5-dioxa-2,4-dioxoundecane, 2,2-hydroxymethyl-1,3-dioxane4,6-dione and 1,3-cyclohexadione. Odor blockers are disclosed in more detail in U.S. Pat. Nos. 4,009,253; 4,187,251; 4,719,105; 5,441,727; and 5,861,371.

Reactive Aldehydes

As an optional odor control agent, reactive aldehydes can be used as an odor control agent to mitigate the effects of malodors. Non-limiting examples of suitable reactive aldehydes include Class I aldehydes, Class II aldehydes, and mixtures thereof. Non-limiting examples of Class I aldehydes include anisic aldehyde, o-allyl-vanillin, benzaldehyde, cuminic aldehyde, ethyl-aubepin, ethyl-vanillin, heliotropin, tolyl aldehyde, and vanillin. Non-limiting examples of Class II aldehydes include 3-(4'-tert.butylphenyl)propanal, 2-methyl-3-(4'-tert.butylphenyl)propanal, 2-methyl-3-(4'-isopropylphenyl)propanal, 2,2-dimethyl-3-(4-ethylphenyl)propanal, cinnamic aldehyde, α-amyl-cinnamic aldehyde, and α-hexyl-cinnamic aldehyde. These reactive aldehydes are described in more detail in U.S. Pat. No. 5,676,163.

Reactive aldehydes, when used, can include a combination of at least two aldehydes, with one aldehyde being selected from acyclic aliphatic aldehydes, non-terpenic aliphatic aldehydes, non-terpenic alicyclic aldehydes, terpenic aldehydes, aliphatic aldehydes substituted by an aromatic group and bifunctional aldehydes; and the second aldehyde being selected from aldehydes possessing an unsaturation alpha to the aldehyde function conjugated with an aromatic ring, and aldehydes in which the aldehyde group is on an aromatic ring. This combination of at least two aldehydes is described in more detail in International Patent Application Pub. No. WO 00/49120.

As used herein, the term "reactive aldehydes" further encompasses deodorizing materials that are the reaction products of (i) an aldehyde with an alcohol, (ii) a ketone with an alcohol, or (iii) an aldehyde with the same or different aldehydes. Such deodorizing materials can be: (a) an acetal or hemiacetal produced by means of reacting an aldehyde with a carbinol; (b) a ketal or hemiketal produced by means of reacting a ketone with a carbinol; (c) a cyclic triacetal or a mixed cyclic triacetal of at least two aldehydes, or a mixture of any of these acetals, hemiacetals, ketals, hemiketals, or cyclic triacetals. These deodorizing perfume materials are described in more detail in International Patent Application Pub. No. WO 01/07095.

Flavanoids

Flavanoids can also be used as an odor control agent. Flavanoids are compounds based on the $C_6 \cdot C_3 \cdot C_6$ flavan skeleton. Flavanoids can be found in typical essential oils. Such oils include essential oil extracted by dry distillation from needle leaf trees and grasses such as cedar, Japanese cypress, eucalyptus, Japanese red pine, dandelion, low striped bamboo and cranesbill and can contain terpenic material such as alpha-pinene, beta-pinene, myrcene, phencone and camphene. Also included are extracts from tea leaf. Descriptions of such materials can be found in JP 02284997 and JP 04030855.

Metallic Salts

The odor control agent of the present invention can include metallic salts for malodor control benefits. The metallic salts are selected from the group consisting of copper salts, zinc salts, and mixtures thereof.

The preferred zinc salts possess malodor control abilities. Zinc has been used most often for its ability to ameliorate malodor, e.g., in mouth wash products, as disclosed in U.S. Pat. Nos. 4,325,939 and 4,469,674. Highly-ionized and soluble zinc salts such as zinc chloride, provide the best source of zinc ions. Preferred zinc salts are selected from the group consisting of zinc borate, zinc caprylate, zinc chloride, zinc ricinoleate, zinc sulfate heptahydrate, zinc undecylenate, and mixtures thereof.

Preferably the metallic salts are water-soluble zinc salts, copper salts or mixtures thereof, and more preferably zinc salts, especially $ZnCl_2$. These salts are preferably present in the present invention as an odor control agent primarily to absorb amine and sulfur-containing compounds. Low molecular weight sulfur-containing materials, e.g., sulfide and mercaptans, are components of many types of malodors, e.g., food odors (garlic, onion), body/perspiration odor, breath odor, etc. Low molecular weight amines are also components of many malodors, e.g., food odors, body odors, urine, etc.

Zinc salts, when used, can be combined with an anionic surfactant having the formula R—(O—CH$_2$—CH$_2$)$_x$—O—CH$_2$COO—, wherein R is a fatty alcohol substituent or an alkylaryl substituent and X is at least 2. Such anionic surfactants can act as a control release agent for the zinc salts to improve the malodor control properties of the composition. This combination of zinc salts and anionic surfactant is described in more detail in U.S. Pat. No. 6,358,469.

Zinc salts, when used, can also be combined with carbonate and/or bicarbonate to improve the malodor control properties of the composition. When zinc salts are combined with carbonate and/or bicarbonate, the composition preferably further comprises a stabilizing anion selected from phosphates having more than one —(P=O)— group and organic acids having more than one acid functionality. This combination of zinc salts, carbonate and/or bicarbonate, and stabilizing anions is described in more detail in U.S. Pat. No. 6,015,547.

Copper salts possess some malodor control abilities. See U.S. Pat. No. 3,172,817, Leupold, et al., which discloses deodorizing compositions for treating disposable articles, comprising at least slightly water-soluble salts of acylacetone, including copper salts and zinc salts.

When metallic salts are added to the composition of the present invention as an odor control agent, they are typically present at a level of from about 0.001% to an effective amount to provide a saturated salt solution, preferably from about 0.002% to about 25%, more preferably from about 0.003% to about 8%, still more preferably from about 0.1% to about 5% by weight of the composition.

Zeolites

The odor control agents herein can also be zeolites. A preferred class of zeolites is characterized as "intermediate" silicate/aluminate zeolites. The intermediate zeolites are characterized by $SiO_2/AlO_2$ molar ratios of less than about 10. Preferably the molar ratio of $SiO_2/AlO_2$ ranges from about 2 to about 10. The intermediate zeolites can have an advantage over the "high" zeolites. The intermediate zeolites have a higher affinity for amine-type odors, they are more weight efficient for odor absorption because they have a larger surface area, and they are more moisture tolerant and retain more of their odor absorbing capacity in water than the high zeolites. A wide variety of intermediate zeolites suitable for use herein are commercially available as Valfor® CP301-68, Valfor® 300-63, Valfor® CP300-35, and Valfor® CP300-56, available from PQ Corporation, and the CBV100® series of zeolites from Conteka.

Zeolite materials marketed under the trade name Abscents® and Smellrite®, available from The Union Carbide Corporation and UOP are also preferred. Such materials are preferred over the intermediate zeolites for control of sulfur-containing odors, e.g., thiols, mercaptans.

When zeolites are used as odor control agents in compositions that are to be sprayed onto surfaces, the zeolite material preferably has a particle size of less than about 10 microns and is present in the composition at a level of less than about 1% by weight of the composition.

Activated Carbon

Activated carbon is another suitable odor control agent for incorporation in the present compositions. The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such trade names as; Calgon-Type CPG®; Type PCB®; Type SGL®; Type CAL®; and Type OL®.

When activated carbon is used as an odor control agent in compositions that are to be sprayed onto surfaces, the activated carbon preferably has a particle size of less than about 10 microns and is present in the composition at a level of less than about 1% by weight of the composition.

To the extent any material described herein as an odor control agent might also be classified as another component described herein, for purposes of the present invention, such material shall be classified as an odor control agent.

Solvents

The present compositions can further comprise optional solvents. Solvents can help to provide compositions that dry more quickly after being applied to surfaces, versus compositions that do not contain solvent. Where it is desirable to have a composition that quickly dries after being applied to a surface, the present compositions preferably further comprise solvents. Suitable solvents herein include monohydric and polyhydric alcohols. Monohydric alcohols useful as solvents in the present composition include ethanol, n-propanol, isopropanol, mixtures thereof, and the like. Polyhydric alcohols useful as solvents in the present composition include glycols such as ethylene glycol, diethylene glycol, triethylene glycol, propylene glycol, dipropylene glycol, glycerine, mixtures thereof, and the like. Other suitable solvents include water-miscible ethers, water-miscible glycol ethers, and propylene glycol monomethyl ether acetate. Non-limiting examples of water-miscible ethers include diethylene glycol diethylether, diethyleneglycol dimethylether, propylene glycol dimethylether, and mixtures thereof. Non-limiting examples of water-miscible glycol ethers include propylene glycol monomethylether, propylene glycol monoethylether, propylene glycol monopropylether, propylene glycol monobutylether, ethylene glycol monobutylether, dipropylene glycol monomethylether, diethyleneglycol monobutylether, and mixtures thereof.

When present, the level of solvent in the present compositions is generally from about 0.1% to about 99.9%, preferably from about 0.5% to about 99%, and more preferably from about 1% to about 90%. If the compositions are spray compositions (especially non-aerosol), the level of alcohol is preferably less than about 35%, more preferably less than about 20%, and even more preferably less than about 10%, by weight of the composition.

Aerosol Propellants

Wherein the present compositions are in the form of an aerosol spray composition, the compositions further comprise an aerosol propellant. Non-limiting examples of suitable aerosol propellants for aerosol compositions herein include aliphatic hydrocarbons such as butane, isobutane, and propane; low molecular weight halogenated hydrocarbons (preferably chlorinated and/or fluorinated hydrocarbons) such as chlorodifluoromethane; dissolvable gases such as carbon dioxide; nitrogen gas; compressed air; and other materials well known in the art.

When present, aerosol propellants are typically incorporated in the present compositions at a level of from about 2% to about 60%, preferably from about 3% to about 50%, by weight of the composition.

Aerosol propellants especially suitable for incorporation in the present compositions are described in detail in U.S. Pat. No. 4,520,142.

Surfactants

To improve the ability of the present compositions to "wet" the surfaces being treated (i.e. improve the ability of the composition to spread across the surface), the compositions preferably further comprise optional surfactants. Preferably, the compositions comprise a surfactant, or mixtures of surfactants, at a level of from about 0.001% to about 90%, preferably from about 0.01% to about 80%, and more preferably from about 0.05% to about 70%, by weight of the composition. If the composition is intended to be sprayed onto the surface via a spray dispenser, the compositions preferably include optional surfactants at a level of less than about 5%, preferably less than about 3%, and more preferably less than about 1%, by weight of the composition.

Surfactants are generally well-known in the detergent art. Surfactants which are suitable in the compositions of the present invention include anionic, nonionic, cationic, amphoteric, zwitterionic, and mixtures of the above types.

Preferred surfactants are described in detail in U.S. Patent Application Pub. No. US 2002/0011584 A1.

Anionic Surfactants

Anionic surfactants can optionally be incorporated in the present compositions. Many suitable nonlimiting examples from the class of anionic surfactants can be found in *Surfactants and Interfacial Phenomena*, 2$^{nd}$ Ed., Milton J. Rosen, 1989, John Wiley & Sons, Inc., pp. 7-16. Additional suitable nonlimiting examples of anionic surfactants can be found in *Handbook of Surfactants*, M. R. Porter, 1991, Blackie & Son Ltd, pp. 54-115 and references therein.

Structurally, suitable anionic surfactants contain at least one hydrophobic moiety and at least one hydrophilic moiety. The surfactant can contain multiple hydrophobic moieties and/or multiple hydrophilic moieties, but preferably less than or equal to about 2 hydrophobic moieties and less than or equal to about 3 hydrophilic moieties. The hydrophobic moiety is typically comprised of hydrocarbons either as an alkyl group or an alkyl-aryl group. Alkyl groups typically contain from about 6 to about 22 carbons, preferably about 10 to about 18 carbons, and more preferably from about 12 to about 16 carbons; aryl groups typically contain alkyl groups containing from about 4 to about 6 carbons. Each alkyl group can be a branched or linear chain and is either saturated or unsaturated. A typical aryl group is benzene. Some typical hydrophilic groups for anionic surfactants include but are not limited to $-CO_2^-$, $-OSO_3^-$, $-SO_3^-$, $-(OR_1)_x-CO_2^-$, $-(OR_1)_x-OSO_3^-$, $-(OR_1)_x-SO_3^-$ where x is being less than about 10 and preferably less than about 5. Some nonlimiting examples of suitable surfactants includes, Stepanol® WAC, Biosoft® 40 (Stepan Co., Northfield, Ill.).

Anionic surfactants can also be created by sulfating or sulfonating animal or vegetable based oils. An example of these type of surfactants include sulfated canola oil and sulfated castor oil (Freedom SCO-75) available from the Freedom Chemical Co., Charlotte N.C. (owned by BF Goodrich).

Non-limiting examples of suitable anionic surfactants include salts of $C_8$-$C_{22}$ alkyl fatty acids; $C_{10}$-$C_{14}$ alkylbenzene sulfonates; $C_{10}$-$C_{22}$ alkene sulfonates; $C_{10}$-$C_{22}$ alkyl ether sulfonates; $C_{10}$-$C_{22}$ alkyl sulfates; $C_4$-$C_{10}$ dialkyl sulfosuccinates; $C_{10}$-$C_{22}$ acyl methionates; alkyl diphenyloxide sulfonates; alkyl naphthalene sulfonates; 2-acetamido hexadecane sulfonates; alkyl glyceryl ether sulfonates; and N-alkyl substituted succinates. Anionic surfactants which are water-soluble alkylbenzene sulfonate salts of organic sulfur-reaction products are described in U.S. Pat. Nos. 2,220,099 and 2,477,383. Especially valuable are linear straight-chain alkylbenzene sulfonates in which the average number of carbon atoms in the alkyl group is from about 11 to 13, abbreviated as $C_{11}$-$C_{13}$ LAS. Other anionic surfactants are described in U.S. Pat. No. 6,358,469, which are preferred when the present compositions comprise zinc salts in combination with carbonate and/or bicarbonate.

When the present compositions comprise uncomplexed cyclodextrin as an odor control agent, the anionic surfactant is preferably cyclodextrin-compatible, meaning that the surfactant does not tend to form complexes with cyclodextrin. Non-limiting examples of cyclodextrin-compatible anionic surfactants are the alkyldiphenyl oxide disulfonates, having the general formula:

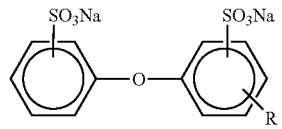

wherein R is an alkyl group. Examples of this type of surfactants are available from the Dow Chemical Company under the trade name Dowfax® wherein R is a linear or branched $C_6$-$C_{16}$ alkyl group. An example of these cyclodextrin-compatible anionic surfactant is Dowfax 3B2 with R being approximately a linear $C_{10}$ group.

Nonionic Surfactants

The present compositions can optionally comprise nonionic surfactants, which are the preferred surfactants in the present compositions. Non-limiting examples of suitable nonionic surfactants include alkyl ethoxylated surfactants, block copolymer surfactants, castor oil surfactants, sorbitan ester surfactants, polyethoxylated fatty alcohol surfactants, glycerol mono-fatty acid ester surfactants, polyethylene glycol fatty acid ester surfactants, and mixtures thereof. These nonionic surfactants are described in more detail in U.S. Patent Application Pub. No. US 2002/0011584 A1.

Alkyl ethoxylated surfactants and castor oil surfactants are preferred nonionic surfactants. Castor oil surfactants include polyoxyethylene castor oil ethers or polyoxyethylene hardened castor oil ethers, which are either partially or fully hydrogenated. Preferred hydrogenated castor oil surfactants are commerically available from Nikko under the trade names HCO 40 and HCO 60 and from BASF under the trade names Cremphor™ RH 40, RH 60, and CO 60.

Cationic Surfactants

Cationic surfactants can also be incorporated in the present compositions. Cationic surfactants, when used in aqueous compositions to be sprayed on fabrics, can improve the ability of the composition to penetrate in between the fibers of the fabrics, which can lead to better performance in terms of reducing malodor and/or reducing the appearance of wrinkles on fabrics. Also, cationic surfactants can be useful to soften fabrics treated with the present compositions.

Suitable cationic surfactants include a wide variety of quaternary compounds. Preferred cationic surfactants are diester quaternary ammonium compounds ("DEQA"). These and other preferred quaternary compounds are described in detail in U.S. Patent Application Pub. No. US 2002/0011584 A1.

To the extent that a cationic surfactant acts as either an antimicrobial active or preservative, for purposes of the present invention, it shall be classified as an antimicrobial active/preservative, as described infra.

Amphoteric Surfactants

Amphoteric surfactants can also be used in the present compositions. Amphoteric surfactants, also called ampholytic surfactants, may be broadly defined as aliphatic derivatives of secondary or tertiary amines, or aliphatic derivatives of heterocyclic secondary and tertiary amines in which the aliphatic radical can be straight chain or branched, and wherein one of the aliphatic substituents contains from about 8 to about 18 carbon atoms and at least one contains an anionic water-solubilizing group, e.g. carboxy, surfate, or sulfonate. Examples of suitable amphoteric surfactants can be found in U.S. Pat. No. 3,929,678 at column 19, lines 18-35.

Zwitterionic Surfactants

The present compositions can optionally comprise zwitterionic surfactants. Zwitterionic surfactants may be broadly described as derivatives of secondary and tertiary amines, derivatives of heterocyclic secondary and tertiary amines, or derivatives of quaternary ammonium, quaternary phosphonium, or tertiary sulfonium compounds.

Free Perfume

The stable, aqueous compositions of the present invention preferably comprise free perfume as an optional ingredient. As used herein, the term "free perfume" refers to perfume that is in the composition, but is not contained within microcapsules. Free perfume is desirable in the present compositions to provide a freshness impression on the surface being treated by the stable, aqueous compositions of the present invention. Free perfume is especially desired in compositions for treating fabrics, since it is important to provide a freshness impression on fabrics, especially clothing. Free perfume can be desirable to provide an immediate "burst" of perfume scent when the composition is applied to a surface, such as by spraying the composition on fabric, upholstered surfaces, or carpeting.

Suitable perfume materials for incorporation in the present compositions are disclosed, e.g., in U.S. Pat. No. 5,939,060 issued Aug. 17, 1999 to Trinh et al. at col. 2, line 38 to col. 7, line 53.

If free perfume is included in the stable, aqueous compositions of the present invention, it can be included at a wide variety of levels. Free perfume is typically at the level from about 0.0001% to about 10%, preferably from about 0.001% to about 7%, and more preferably from about 0.01% to about 5%, by weight of the composition.

Antimicrobial Actives/Preservatives

The present compositions can optionally further comprise antimicrobial actives/preservatives. As discussed hereinbefore, antimicrobial actives can constitute the active material contained in the microcapsules of the present compositions. In addition or alternatively, the present compositions can comprise free antimicrobial actives/preservatives, meaning antimicrobial actives/preservatives that are not contained within the microcapsules of the present compositions.

Antimicrobial actives/preservatives suitable for incorporation in the present compositions include many quaternary compounds, biguanide compounds, and other antimicrobial actives having antimicrobial efficacy. These materials can be incorporated in the present compositions in an effective amount to inhibit the growth of microorganisms in the compositions themselves (i.e. act as a preservative) and/or to kill microorganisms on the surfaces being treated with the present compositions (i.e. act as an antimicrobial active).

Suitable antimicrobial actives/preservatives herein include quaternary compounds, biguanide compounds, and mixtures thereof. Non-limiting examples of quaternary compounds include benzalkonium chlorides and/or substituted benzalkonium chlorides such as commercially available Barquat® (available from Lonza), Maquat® (available from Mason), Variquat® (available from Witco/Sherex), and Hyamine® (available from Lonza); di($C_6$-$C_{14}$)alkyl di short chain ($C_{1-4}$ alkyl and/or hydroxyaml) quaternary such as Bardac® products of Lonza; N-(3-chloroallyl) hexaminium chlorides such as Dowicide® and Dowicil® available from Dow; benzethonium chloride such as Hyamine® from Rohm & Haas; methylbenzethonium chloride represented by Hyamine® 10X supplied by Rohm & Haas, cetylpyridinium chloride such as Cepacol chloride available from of Merrell Labs; and diester quaternary ammonium compounds. Examples of preferred dialkyl quaternary compounds are di($C_8$-$C_{12}$)dialkyl dimethyl ammonium chloride, such as didecyldimethylammonium chloride (Bardac® 22), and dioctyldimethylammonium chloride (Bardac® 2050). The quaternary compounds useful as cationic preservatives and/or antimicrobial agents herein are preferably selected from the group consisting of dialkyldimethylammonium chlorides, alkyldimethylbenzylammonium chlorides, dialkylmethylbenzylammonium chlorides, and mixtures thereof. Other preferred cationic antimicrobial actives useful herein include diisobutylphenoxyethoxyethyl dimethylbenzylammonium chloride (commercially available under the trade name Hyamine® 1622 from Rohm & Haas) and (methyl)diisobutylphenoxyethoxyethyl dimethylbenzylammonium chloride (i.e. methylbenzethonium chloride).

Non-limiting examples of biguanide compounds include 1,1'-hexamethylene bis(5-(p-chlorophenyl)biguanide), commonly known as chlorhexidine, and Cosmoci® CQ®, Vantocil® IB, including poly (hexamethylene biguanide) hydrochloride. Other useful antimicrobial actives include the bis-biguanide alkanes. Usable water soluble salts of the above are chlorides, bromides, sulfates, alkyl sulfonates such as methyl sulfonate and ethyl sulfonate, phenylsulfonates such as p-methylphenyl sulfonates, nitrates, acetates, gluconates, and the like.

Non-limiting examples of other suitable antimicrobial actives include Pyrithiones (especially the zinc complex (ZPT)), Octopirox®, Dimethyldimethylol Hydantoin (Glydant®), Sodium Sulfite, Sodium Bisulfite, Imidazolidinyl Urea (Germall 115®), Diazolidinyl Urea (Germall II®), Benzyl Alcohol, 2-Bromo-2-nitropropane-1,3-diol (Bronopol®), Formalin (formaldehyde), Iodopropenyl Butylcarbamate (Polyphase P100®), Chloroacetamide, Methanamine, Methyldibromonitrile Glutaronitrile (1,2-Dibromo-2,4-dicyanobutane or Tektamer®), Glutaraldehyde, 5-bromo-5-nitro-1,3-dioxane (Bronidox®), Phenethyl Alcohol, o-Phenylphenol/sodium o-phenylphenol, Sodium Hydroxymethylglycinate (Suttocide A®), Polymethoxy Bicyclic Oxazolidine (Nuosept C®), Dimethoxane, Thimersal, Dichlorobenzyl Alcohol, Captan, Chlorphenenesin, Dichlorophene, Chlorbutanol, Glyceryl Laurate, Halogenated Diphenyl Ethers, 2,4,4'-trichloro-2'-hydroxy-diphenyl ether (Triclosan® or TCS), 2,2'-dihydroxy-5,5'-dibromo-diphenyl ether, Phenolic Compounds (as described in U.S. Pat. No. 6,190,674), Para-chloro-meta-xylenol (PCMX), Chlorothymol, Phenoxyethanol, Phenoxyisopropanol, 5-Chloro-2-hydroxydiphenylmethane, Resorcinol and its Derivatives (as described in U.S. Pat. No. 6,190,674), 5-Chloro 2,4-Dihydroxydiphenyl Methane, 4'-Chloro 2,4-Dihydroxydiphenyl Methane, 5-Bromo 2,4-Dihydroxydiphenyl Methane, 4'-Bromo 2,4-Dihydroxydiphenyl Methane, Bisphenolic Compounds (as described in U.S. Pat. No. 6,190,674), Parabens (as described in U.S. Pat. No. 6,190,674), Halogenated Carbanilides (as described in U.S. Pat. No. 6,190,674), and mixtures thereof.

Antimicrobial actives, when present in the compositions of the present invention, are included at an effective amount to kill microorganisms on the surface being treated with the compositions, typically at a level of from about 0.001% to about 20%, preferably from about 0.01% to about 10%, and more preferably from about 0.05% to about 5%, by weight of the composition.

Wrinkle Control Agents

The present compositions can optionally further comprise a wrinkle control agent, wherein the wrinkle control agent helps to prevent and/or control wrinkles from forming in surfaces treated with the present compositions, especially fabrics. Wrinkle control agents useful herein include fiber lubricant, shape retention polymer, hydrophilic plasticizer, lithium salt, and mixtures thereof. Such wrinkle control agents are described in detail in U.S. Pat. No. 6,001,343 issued Dec. 14, 1999 to Trinh et al. Wrinkle control compositions that can be suitable as base compositions of the present invention that comprise microcapsules containing an active material, especially compositions that can be used in a cabinet-type or bag-type apparatus for conditioning garments, are also disclosed in co-pending U.S. application Ser. No. 09/674,224 filed Apr. 27, 1998 by Hubesch et al. (which relates to WO 99/55950 published Nov. 4, 1999); and co-pending U.S. application Ser. No. 09/673,600 filed Apr. 27, 1998 by Woo et al. (which relates to WO 99/55816 published Nov. 4, 1999).

Other additional optional ingredients can be included in the present compositions. Non-limiting examples of additional optional ingredients include brighteners, colorants, and the like.

The present compositions will typically have a pH of from about 2 to about 10, preferably from about 3 to about 9.5, and more preferably from about 3.5 to about 9. Depending on the materials included in the composition, it can be desirable to adjust the pH of the composition to be acidic or alkaline. For example, if the composition contains an acid activated dispersant (e.g. acrylate/aminoacrylate copolymers such as ALCOGUM® L-511), the composition preferably has a pH of less than about 8, preferably less than about 7.5, and more preferably less than about 7. On the other hand, for example, if the composition contains an alkali activated dispersant (e.g. acrylate/acrylic polymers such as ALCOGUM® SL-70), the composition preferably has a pH of greater than about 4, preferably greater than about 5, and more preferably greater than about 5.5.

The compositions of the present invention can be in the form of aqueous liquids (e.g. fabric refreshers such as those described in U.S. Pat. No. 6,146,621), aerosols (such as those described in U.S. Pat. No. 4,520,142), gels (e.g. automatic dishwashing gels such as those described in U.S. Pat. No. 5,384,061), pastes (e.g. toothpaste such as those described in U.S. Pat. No. 4,701,319), lotions (e.g. skin lotions such as those described in U.S. Pat. No. 5,968,258), powder detergent granules (e.g. laundry detergent compositions such as those described in U.S. Pat. No. 5,338,476), shampoo/conditioners (such as those described in U.S. Pat. No. 6,221,817), bar soaps (such as those described in U.S. Pat. No. 5,254,281), and the like. The compositions can also be incorporated in substrates such as fabric softener dryer sheets (see, e.g., U.S. Pat. No. 4,808,086), premoistened sheets for at-home dry cleaning processes (see, e.g., U.S. Pat. No. 5,630,848), pre-moistened cleaning wipes (see, e.g., U.S. Pat. No. 6,183,763), dry dusting sheets (see, e.g., U.S. Pat. No. 5,525,397); and diapers (see, e.g., U.S. Pat. No. 6,319,239). The compositions can also be incorporated in plug-in type air fresheners (such as those described in U.S. Pat. No. 5,976,503). Preferably, the present compositions are aqueous liquids, especially those comprising relatively high amounts of water.

The preferred methods of the present invention relate to treating surfaces, preferably fabrics, with the stable, aqueous compositions of the present invention comprising the step of contacting the surface with the stable, aqueous composition. As used herein, the term "fabrics" is meant to encompass a variety of fabrics and articles composed of fabric and/or fibers, including but not limited to clothes, curtains, drapes, upholstered furniture, carpeting, bed linens, bath linens, tablecloths, sleeping bags, tents, car interior (e.g., car carpet, fabric car seats), and the like. The methods more specifically relate to reducing malodor impression on surfaces, especially fabrics, and/or reducing the appearance of wrinkles on fabrics. The surfaces are preferably treated by either spraying dilute aqueous compositions of the present invention onto the surfaces via a spray dispenser, or by adding the concentrated compositions of the present invention to, for example, a wash and/or rinse cycle in a typical laundry process.

A preferred method herein includes a method of reducing malodor impression on a surface (preferably fabrics) having malodor impression, the method comprising the step of contacting the surface with a stable, aqueous composition as described hereinbefore.

The composition for reducing malodor impression herein can be used by distributing, e.g., by placing the aqueous solution into a dispensing means, preferably a spray dispenser and spraying an effective amount onto the desired surface or article. An effective amount as defined herein means an amount sufficient to absorb odor to the point that it is not discernible by the human sense of smell yet not so much as to saturate or create a pool of liquid on said article or surface and so that when dry there is no visual deposit readily discernible. Distribution can be achieved by using a spray device, a roller, a pad, etc. For odor control, an effective amount, as defined herein, means an amount sufficient to absorb odor to effect a noticeable reduction in the perceived odor, preferably to the point that it is not discernible, by the human sense of smell.

The present invention encompasses the method of spraying an effective amount of the composition for reducing malodor onto household surfaces. Preferably said household surfaces are selected from the group consisting of countertops, cabinets, walls, floors, bathroom surfaces and kitchen surfaces.

Additional methods include, for example, adding the aqueous liquid composition to a steam iron and then using the steam iron to iron fabrics. Another method includes adding the aqueous liquid composition to a device for refreshing fabrics (such as that described in International Patent Application Pub. No. WO 02/14594).

When the present compositions include a wrinkle control agent, methods of controlling wrinkles in fabrics are encompassed by the present invention as described in detail in co-pending U.S. Patent Application Pub. No. US 2002/0011584 A1.

The compositions of the present invention can be packaged in a wide variety of packages well known in the art. When the present compositions are aqueous liquid compositions, the compositions are preferably packaged in a spray dispenser. Suitable spray dispensers can be manually operated or non-manually operated (e.g. battery-powered spray dispensers). Suitable spray dispensers are described in detail in U.S. Pat. No. 6,284,231. When aerosol compositions are created, they are typically packaged in an aerosol spray dispenser, such as those described in U.S. Pat. Nos. 3,436,772 and 3,600,325. Other suitable spray dispensers are described in more detail in U.S. Pat. Nos. 4,082,223; 4,161,288; 4,434,917; 4,819,835; and 5,303,867.

The stable, aqueous compositions herein (especially concentrated compositions) can also be packaged in a bottle, especially a bottle that comprises a measuring closure. The measuring closure provides a convenient means to dispense the appropriate amount of the composition, especially when dispensing concentrated compositions into a wash and/or rinse solution containing fabrics to be treated in a typical laundry process. The bottle also preferably comprises a drain-back spout, which permits the composition to be dispensed more easily and with less mess. Non-limiting examples of suitable bottles are described in detail in U.S. Pat. No. 4,666,065 issued May 19, 1987 to Ohren; U.S. Pat. No. 4,696,416 issued Sep. 29, 1987 to Muckenfuhs et al.; and U.S. Pat. No. 4,981,239 issued Jan. 1, 1991 to Cappel et al.

The present compositions are made by mixing together the ingredients comprising the composition. A preferred process for making a composition of the present invention is described in Example 15.

The following are non-limiting examples of the present invention.

EXAMPLES

| Component | Ex 1 | Ex 2 | Ex 3 | Ex 4 | Ex 5 | Ex 6 | Ex 7 | Ex 8 |
|---|---|---|---|---|---|---|---|---|
| Water | To 100 | To 100 | To 100 | To 100 | To 100 | To 100 | To 100 | To 100 |
| Poly(oxymethyleneurea) microcapsules | 0.1 | | | 0.15 | 0.1 | | 0.2 | |
| Poly(oxymethyleneurea) microcapsules containing odor control agents | | | | 0.05 | 0.1 | | | 0.1 |
| Poly(oxymethylenemelamine) microcapsules | | 0.15 | | | | 0.1 | | |
| Gelatine microcapsules | | | 0.2 | | | | | |
| Polyurethane microcapsules | | | | | | | | 0.05 |
| Acrylic Polymer | 0.35 | 0.1 | 0.05 | | | 0.05 | | 0.3 |
| Water Swellable Clay | | | | | | 0.65 | 1.00 | |
| Fumed Silica | | | | | 0.5 | | | |
| Gellan Gum | | | | 0.03 | | | | |
| Diethylene Glycol | 0.1 | | | 0.1 | | | | |
| Polyalkyleneoxide modified polydimethylsiloxane | 0.1 | 0.1 | 0.1 | 0.1 | 0.1 | 0.1 | 0.1 | 0.1 |
| Ethoxylated, Hydrogenated Castor Oil | | 0.1 | 0.2 | 0.1 | 0.2 | | 0.1 | 0.05 |
| Perfume | 0.1 | 0.05 | | 0.065 | 0.12 | 0.1 | 0.03 | 0.03 |
| Hydroxypropyl beta-cyclodextrin | 1.1 | 0.9 | | 1.0 | | 1.0 | | |
| Methylated beta-cyclodextrin | | | 1.1 | | 1.0 | | 1.0 | 0.9 |
| Ethanol | 3 | 3 | 3 | 3 | 3 | 5 | 3 | 3 |
| Citric Acid | | | | | | | 0.07 | |

| Component | Ex 9 | Ex 10 | Ex 11 | Ex 12 | Ex 13 | Ex 14 |
|---|---|---|---|---|---|---|
| Water | To 100 | To 100 | To 100 | To 100 | To 100 | To 100 |
| Poly(oxymethyleneurea) microcapsules | 0.1 | | | | 0.05 | |
| Poly(oxymethylenemelamine) microcapsules | | 0.15 | | | | 0.07 |
| Gelatine microcapsules | | | 0.05 | | | |
| Polyurethane microcapsules | | | | 0.1 | | |
| Diethylene Glycol | 0.25 | | | 0.1 | 0.1 | |
| Polyalkyleneoxide modified polydimethylsiloxane | 0.1 | 0.1 | 0.1 | 0.1 | 0.1 | 0.1 |
| Ethoxylated, Hydrogenated Castor Oil | 0.1 | 0.1 | 0.2 | 0.05 | | 0.1 |
| Didecyl-dimethylammonium chloride | 0.139 | 0.139 | 0.125 | | 0.125 | |
| Perfume | 0.05 | 0.025 | 0.010 | 0.03 | 0.03 | 0.05 |
| Hydroxypropyl beta-cyclodextrin | | | | | 1.0 | |
| Methylated beta-cyclodextrin | 1.00 | 1.00 | 1.00 | 1.1 | | 1.0 |
| Ethanol | 3 | 3 | 5 | 3 | 30 | 20 |
| Acrylates/Aminoacrylates Copolymer | 0.75 | 0.5 | 0.25 | 0.35 | 0.2 | |
| Citric Acid | | 0.1 | 0.2 | | | |
| Lactic Acid | 0.2 | 0.1 | | 0.1 | 0.05 | |
| Aerosol Propellant | | | | | 20 | 40 |

For each composition in the above Examples 1-14, the pH of each composition is adjusted as needed between 3 and 11 with sodium hydroxide or hydrochloric acid. The microcapsules in each of the above Examples 1-14 contain from about 0.001% to about 99.9%, by weight of the total microcapsule, of an active material selected from the group consisting of perfumes, flavoring agents, fungicide, brighteners, antistatic agents, wrinkle control agents, fabric softener actives, hard surface cleaning actives, skin and/or hair conditioning agents, antimicrobial actives, UV protection agents, insect repellants, animal/vermin repellants, flame retardants, and mixtures thereof.

EXAMPLE 15

A one kilogram batch of the composition of Example 9 is made as follows. A mixer is used to blend the ingredients of the composition in a four liter beaker. The mixer has a 4" pitch blade and the mixing speed of the mixer is set at 150 RPM. The following ingredients are added to the four liter beaker in sequential order: 914.26 grams of water; 32.50 grams of ethanol; 1.11 grams of microcapsules containing perfume; 2.50 grams of diethylene glycol; 2.78 grams of Bardac® 2250; 1.00 grams of Silwet® L-7600; 1.00 grams of Cremophor™ CO-60; 0.25 grams of free perfume. These ingredients are allowed to mix for 5 minutes. Then 19.88 grams of methylated beta-cyclodextrin are added to the beaker. Then 22.50 grams of Alcogum® L-511 are added to the beaker. 2.22 grams of lactic acid are then slowly added to the beaker dropwise. The mixture is then allowed to mix for an additional 10 minutes. The resulting composition will have a pH of about 4.

While particular embodiments of the present invention have been illustrated and described, it would be apparent to those skilled in the art that various other changes and modifications can be made without departing from the spirit and scope of the invention. It is therefore intended to cover in the appended claims all such changes and modifications that are within the scope of this invention.

What is claimed is:

1. A method of providing a controlled-release of an active material onto a surface, said method comprising the step of contacting said surface with a non-aerosol composition comprising:
   (a) from about 0.001% to about 1%, by weight of said composition, of microcapsules containing at least one of the following:
      (i) an active material, wherein the active material is chosen from the group consisting of: perfumes, fungicide, brighteners, antistatic agents, wrinkle control agents, fabric softener actives, hard surface cleaning actives, skin and/or hair conditioning agents, antimicrobial actives, UV protection agents, and mixtures thereof; and/or
      (ii) an encapsulated odor control agent;
   wherein when both said active material and said odor control agent are used, they are contained in the same microcapsules; in different microcapsules; or both,
      (iii) wherein the active material is free of an insect repellant and an animal/vermin repellant;
   (b) from about 0.001% to about 10%, by weight of the composition, of a dispersant,
   wherein the dispersant is selected from the group consisting of: pectine, alginate, arabinogalactan, carageenan, acrylates/acrylic polymers, water-swellable clays, fumed silicas, acrylate/aminoacrylate copolymers, and mixtures thereof;
   (c) free perfume that is not contained in said microcapsule;
   (d) water, wherein said water is present in said composition at a level of at least about 80% by weight of the composition; and
   (e) less than 1% surfactant;
   wherein said composition is packaged in a spray dispenser and said surface is contacted with said composition by spraying said composition from said spray dispenser onto said surface, wherein said composition does not leave a visible residue on said surface, and further, wherein said microcapsules comprise a material selected from the group consisting of urea-formaldehydes, melamineformaldehydes, phenolformaldehydes, gelatin, poly(vinyl alcohol), poly(vinyl pyrrolidone), polyacrylates, polyamides, polyurethane, polymethacrylates, polyepoxides, cellulose acetate, cellulose nitrate, cellulose acetate butyrate, ethyl cellulose polyester, polychlorotrifluoroethylene, ethyl/vinyl acetate, saran, polystyrene, zein, paraffin wax, animal wax, vegetable wax, microcrystalline wax, polyethylene wax, and mixtures thereof.

2. The method of claim 1 wherein said microcapsules comprise a material selected from the group consisting of poly(oxymethyleneurea), poly(oxymethylenemelamine), gelatin, polyurethane, poly(vinyl alcohol), and mixtures thereof.

3. The method of claim 1 wherein said microcapsules are present in said composition at a level of from about 0.001% to about 0.9% by weight of the composition.

4. The method of claim 3 wherein said microcapsules are present in said composition at a level of from about 0.001% to about 0.5% by weight of the composition.

5. The method of claim 4 wherein said microcapsules are present in said composition at a level of from about 0.001% to about 0.2% by weight of the composition.

6. The method of claim 1 wherein said active material is selected from the group consisting of perfumes, antimicrobial actives, and mixtures thereof.

7. The method of claim 6 wherein said active material is perfume.

8. The method of claim 1 wherein said microcapsules contain said active material at a level of from about 1% to about 99% by weight of the total microcapsule.

9. The method of claim 1 wherein said microcapsule has a particle size of from about 0.001 micron to about 1 millimeter.

10. The method of claim 9 wherein said microcapsule has a particle size of from about 1 micron to about 500 microns; and the dispersant is chosen from acrylates/acrylic polymers, acrylate/aminoacrylate copolymers, and mixtures thereof.

11. The method of claim 10 wherein said microcapsule has a particle size of from about 10 microns to about 100 microns; and wherein the composition is free of cyclodextrin.

12. The method of claim 1 wherein said dispersant is selected from the group consisting of pectine, alginate, arabinogalactan, carageenan, water-swellable clays, fumed silicas, and mixtures thereof.

13. The method of claim 12 wherein said dispersant is selected from the group consisting of fumed silicas, water-swellable clays, and mixtures thereof.

14. The method of claim 13 wherein said dispersant is selected from the group consisting of fumed silicas.

15. The method of claim 13, wherein said dispersant is present in said composition at a level of from about 0.001% to about 1% by weight of the composition, and wherein the dispersant is a water-swellable clay.

16. The method of claim 15 wherein said dispersant is present in said composition at a level of from about 0.001% to about 0.9% by weight of the composition.

17. The method of claim 1 wherein said composition further comprises solvent.

18. The method of claim 17 wherein said solvent is present in said composition at a level of less than about 10% by weight of the composition.

19. The method of claim 1 wherein said composition further comprises an effective amount of antimicrobial active to kill microorganisms on a surface treated with said composition, wherein said antimicrobial active is not contained in said microcapsule.

20. The method of claim 1 wherein said composition further comprises an odor control agent.

21. The method of claim 20 wherein said odor control agent is selected from the group consisting of uncomplexed cyclodextrin; odor blockers; reactive aldehydes; flavanoids; zeolites; activated carbon; and mixtures thereof.

22. The method of claim 1 wherein said surface is fabric.

23. An aerosol composition for providing controlled-release of an active material, said composition comprising:
(a) from about 0.001% to about 1%, by weight of said composition, of microcapsules containing at least one of the following:
  (i) an active material, wherein the active material is perfume; and/or
  (ii) an encapsulated odor control agent;
wherein when both said active material and said odor control agent are used, they are contained in the same microcapsules; in different microcapsules; or both,
  (iii) wherein the microcapsule is free of an animal/vermin repellant and an insect repellant;
(b) from about 0.001% to about 1%, by weight of said composition, of a dispersant; wherein the dispersant is selected from the group consisting of:
acrylates/acrylic polymers, acrylate/aminoacrylate copolymers, and mixtures thereof;
(c) aerosol propellant;
(d) aqueous carrier; and
(e) free perfume that is not contained in said microcapsule;
(f) less than 1% surfactant;
wherein said composition does not leave a visible residue on said surface.

24. A method of providing a controlled-release of an active material onto a surface, said method comprising the step of contacting said surface with a composition according to claim 23.

25. The method of claim 24 wherein said composition is packaged in a spray dispenser and said surface is contacted with said composition by spraying said composition from said spray dispenser onto said surface.

26. The method of claim 25 wherein said surface is fabric.

27. A method of providing a controlled-release of an active material onto a surface, said method comprising the step of contacting said surface with an antimicrobial composition for providing controlled-release of an active material and for killing microorganisms on a surface, said composition comprising:
(a) from about 0.001% to about 1%, by weight of said composition, of microcapsules containing at least one of the following:
  (i) an active material; and/or
  (ii) an encapsulated odor control agent;
wherein when both said active material and said odor control agent are used, they are contained in the same microcapsules; in different microcapsules; or both,
(b) from about 0.001% to about 10%, by weight of the composition, of a dispersant wherein the dispersant is selected from the group consisting of:
acrylates/acrylic polymers, acrylate/aminoacrylate copolymers, and mixtures thereof;
(c) an effective amount of an antimicrobial active to kill microorganisms on said surface, wherein said antimicrobial active is not contained in said microcapsules;
(d) free perfume that is not contained in said microcapsule; and
(e) aqueous carrier,
(f) less than 1% surfactant;
wherein said composition is packaged in a spray dispenser and said surface is contacted with said composition by spraying said composition from said spray dispenser onto said surface, wherein said composition does not leave a visible residue on said surface.

28. The method of claim 27 wherein said antimicrobial active is selected from the group consisting of quaternary compounds, biguanide compounds, pyrithiones, dimethyldimethylol hydantoin, sodium sulfite, sodium bisulfite, imidazolidinyl urea, diazolidinyl urea, benzyl alcohol, 2-bromo-2-nitropropane-1,3-diol, formalin, iodopropenyl butylcarbamate, chloroacetamide, methanamine, methyldibromonitrile glutaronitrile, glutaraldehyde, 5-bromo-5-nitro-1,3-dioxane, phenethyl alcohol, o-Phenylphenol/sodium o-phenylphenol, sodium hydroxymethylglycinate, polymethoxy bicyclic oxazolidine, dimethoxane, thimersal, dichlorobenzyl alcohol, captan, chlorphenenesin, dichlorophene, chlorbutanol, glyceryl laurate, halogenated diphenyl ethers, 2,4,4'-trichloro-2'-hydroxy-diphenyl ether, 2,2'-dihydroxy-5,5'-dibromo-diphenyl ether, phenolic compounds, para-chloro-meta-xylenol, chlorothymol, phenoxyethanol, phenoxyisopropanol, 5-chloro-2-hydroxy-diphenylmethane, resorcinol and its derivatives, 5-chloro 2,4-dihydroxydiphenyl methane, 4'-chloro 2,4-dihydroxydiphenyl methane, 5-bromo 2,4-dihydroxydiphenyl methane, 4'-bromo 2,4-dihydroxydiphenyl methane, bisphenolic compounds, parabens, halogenated carbanilides, and mixtures thereof.

29. The method of claim 27 wherein said antimicrobial active is present in said composition at a level of from about 0.001% to about 20% by weight of the composition.

30. The method of claim 27 wherein said surface is fabric.

* * * * *